(12) United States Patent
Liebetraut et al.

(10) Patent No.: US 12,156,635 B2
(45) Date of Patent: Dec. 3, 2024

(54) ROD LENS SYSTEM

(71) Applicant: Schölly Fiberoptic GmbH, Denzlingen (DE)

(72) Inventors: Peter Liebetraut, Gundelfingen (DE); Hannes Joseph, Bahlingen (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 608 days.

(21) Appl. No.: 17/519,926

(22) Filed: Nov. 5, 2021

(65) Prior Publication Data

US 2022/0146813 A1    May 12, 2022

(30) Foreign Application Priority Data

Nov. 10, 2020   (DE) .......................... 102020129529.4

(51) Int. Cl.
  *A61B 1/00*   (2006.01)
  *A61B 1/055*  (2006.01)
  *G02B 23/24*  (2006.01)
  *G02B 27/00*  (2006.01)

(52) U.S. Cl.
  CPC .......... *A61B 1/00096* (2013.01); *A61B 1/055* (2013.01); *G02B 23/243* (2013.01); *G02B 23/2446* (2013.01); *G02B 23/2484* (2013.01); *G02B 27/005* (2013.01); *G02B 23/2453* (2013.01); *G02B 2207/113* (2013.01)

(58) Field of Classification Search
  CPC . A61B 1/00096; A61B 1/055; A61B 1/00179; G02B 23/243; G02B 23/2446; G02B 23/2484; G02B 27/005; G02B 23/2453; G02B 2207/113; G02B 1/041
  USPC ......................................... 359/642
  See application file for complete search history.

(56) References Cited

U.S. PATENT DOCUMENTS

| | | | |
|---|---|---|---|
| 2015/0238071 A1* | 8/2015 | Hua ...................... | A61B 1/3132 600/109 |
| 2017/0139197 A1* | 5/2017 | Rehe .................. | G02B 27/0025 |
| 2017/0293139 A1* | 10/2017 | Rehe .................... | G02B 23/243 |

FOREIGN PATENT DOCUMENTS

| | | |
|---|---|---|
| DE | 102014107456 | 12/2015 |
| DE | 102016115738 | 3/2018 |
| DE | 102016118746 | 4/2018 |

\* cited by examiner

*Primary Examiner* — Henry Duong
(74) *Attorney, Agent, or Firm* — Volpe Koenig

(57) ABSTRACT

To improve the imaging while simultaneously simplifying the manufacturing of a rigid endoscope (2), an inversion system (1) is used as a relay optical unit for the image transfer from an objective (3) to a proximally arranged camera unit (4) of the endoscope (2). The inversion system has an odd number of a first type A of rod lenses (7) and an even number of a second type B of rod lenses (7), which are each arranged on half of the inversion system (1) with respect to a center plane (9) of the inversion system (1).

15 Claims, 2 Drawing Sheets

ROD LENS SYSTEM

INCORPORATION BY REFERENCE

The following documents are incorporated herein by reference as if fully set forth: German Patent Application No. 10 2020 129 529.4, filed Nov. 10, 2020.

TECHNICAL FIELD

The invention relates to an inversion system for use in an endoscope, which has an objective and a camera unit, wherein the inversion system is designed to relay light from the objective to the camera unit and wherein the inversion system has multiple inversion sets each made up of two rod lenses. These inversion sets each implement an approximately 1:1 imaging here.

The invention furthermore relates to an endoscope which is based on such an inversion system and moreover has an objective and a camera unit. The inversion system is situated just between the objective and the camera unit in this endoscope.

Finally, the invention relates to an intended use of an inversion system in an endoscope.

BACKGROUND

Inversion systems as described at the outset are known in particular in the case of rigid endoscopes, where they are used as relay optical units, typically in the form of a rod lens system, to relay an image distally recorded using an objective along an endoscope shaft to a proximally arranged image sensor. The inversion sets of such inversion systems are moreover typically formed from rod lenses having solely spherical surfaces in the prior art. Two identical or two different rod lenses are often grouped here to form one inversion set, while the rod lenses can have two, three, or more components. The production and assembly, in particular the optical alignment, of such inversion systems can be very complex.

Inversion systems used as relay optical units can thus enlarge the optical length of the image processing system, in particular in endoscopes or applications where the relevant object cannot be observed up close. Relay optical units can also be used to invert the image behind the ocular of an image processing system so that it is displayed correctly.

In known inversion systems, it is furthermore typical to correct different imaging aberrations as much as possible. In particular, correcting longitudinal chromatic aberration (LCA) and transversal chromatic aberration (TCA) is known, thus the deviation of a pixel in the longitudinal or transversal direction as a function of the wavelength of the light.

SUMMARY

Against this background, the invention is based on the object of providing an inversion system producible cost-effectively which may be used in an endoscope to achieve imaging of higher-quality over a broad wavelength range, for example, from the visible range to the infrared range.

To achieve this object, one or more features are provided according to the invention in an inversion system. In particular, it is thus provided according to the invention to achieve the object in an inversion system of the type mentioned at the outset that the inversion system only has a first type A and a second type B of rod lenses, and that a respective inversion set A-A or B-B of the inversion system, which is formed from two rod lenses of the same type, applies a first longitudinal chromatic aberration (LCA1) and a first transversal chromatic aberration (TCA1), wherein an inversion set A-B of the inversion system, which is formed from two rod lenses of different types, applies a second longitudinal chromatic aberration (LCA2) and a second transversal chromatic aberration (TCA2). The first longitudinal chromatic aberration (LCA1) and the second longitudinal chromatic aberration (LCA2) have the same sign here and the first transversal chromatic aberration (TCA1) and the second transversal chromatic aberration (TCA2) have different signs.

By way of this approach, the transversal chromatic aberrations of the individual inversion sets may partially compensate for one another, while the longitudinal chromatic aberrations thereof add up. The total longitudinal chromatic aberration (total LCA=TLCA) of the inversion system may then be compensated for comparatively simply, however, by the optical design of the objective and the optical components of the camera unit.

According to the invention, the transversal chromatic aberrations are thus compensated for continuously along the chain of the inversion steps of the inversion system so that the total transversal chromatic aberration does not increase excessively along the inversion system. This is because otherwise it could only be compensated for with great effort, that is to say using a very large number of optical elements. In contrast to longitudinal chromatic aberrations, transversal chromatic aberrations can be influenced via the ratio of radii of curvature, and this can be done independently of the longitudinal chromatic aberration (LCA). While the LCA can thus be understood as a zeroth order aberration, the transversal chromatic aberration TCA can be understood as a higher order aberration. In simple terms, this is because the transversal chromatic aberration arises due to different wavelengths being enlarged by different amounts, which is dependent in each case on the position of the respective main beam. It is therefore also possible that the different types A and B of rod lenses also generate transversal aberrations of different signs.

In other words, the invention thus provides that—in particular upon restriction to use of simple doublets for the rod lenses of the inversion system—a continuous growth of the longitudinal chromatic aberration is assumed. The TLCA can then be substantially compensated for once by the objective and once by the optical components of the camera unit. Observed from another viewing angle, the inversion system according to the invention can thus be used to compensate for chromatic aberrations, in particular longitudinal chromatic aberrations, of the objective and the camera optical unit of the camera unit of the endoscope.

It is advantageous here that an endoscope which is equipped with the inversion system according to the invention can be color corrected over a large wavelength range, which can comprise, for example, a part of the visible range and the infrared range.

According to the invention, the object can also be achieved by further advantageous embodiments according to the description and claims that follow.

For example, the respective longitudinal chromatic aberrations (LCA1) and the respective transversal chromatic aberrations (TCA1) of inversion sets A-A or B-B of the inversion system, which are each formed from two rod lenses of the same type (A or B), can have the same sign.

Furthermore, an inversion set B-B of the inversion system, which is formed from two rod lenses of the second type B, can apply a third longitudinal chromatic aberration (LCA3) which is less in absolute value than the second longitudinal chromatic aberration (LCA2) and/or is less than the first longitudinal chromatic aberration (LCA1). An inversion set B-B of the inversion system which is formed from two rod lenses of the second type B can furthermore apply a third transversal chromatic aberration (TCA3), which is less in absolute value than the second transversal chromatic aberration (TCA2) and/or is less than the first transversal chromatic aberration (TCA1).

With respect to the transversal chromatic aberration (TCA), this means that, for example, an inversion step A-A can generate a positive TCA, while a mixed inversion step A-B can generate a negative TCA. The inversion system can, however, have two identical inversion steps A-A and only one mixed inversion step A-B. In this case, the inversion step B-B can also be designed so that it generates a negative TCA. The TCA which is generated by two identical inversion steps A-A can thus be at least partially compensated for by following inversion steps A-B and B-B, which use the second type B of rod lens. It can thus be provided that the transversal chromatic aberrations (TCA) of a mixed inversion step A-B and of a further inversion step B-B, which is formed from two rod lenses of the type B, have the same sign. In particular the TCA of the inversion step A-B can be less than that of the inversion step A-A.

Such designs thus significantly increase the possibilities for the compensation of aberrations but maintain the very simple structure of the inversion system. This is because the inversion system can in particular be designed such that all rod lenses of the inversion system are each formed as doublets on the basis of only two different components, which ensures very cost-effective manufacturing of the inversion system. It is preferred here if the rod lenses of the inversion system all apply a positive longitudinal chromatic aberration (LCA1, LCA2, LCA3). This is because the total longitudinal chromatic aberration (TLCA) of the inversion system can then be positive in particular.

The inversion system can furthermore have an odd number of rod lenses of the first type A. Alternatively or additionally, the inversion system can furthermore have an even number of rod lenses of the second type B. Such embodiments can thus in particular have the result that the inversion system comprises an odd number of rod lenses, for example, nine rod lenses. An endoscope in which the inversion system is used can of course in this case also have further rod lenses, for example in the objective or in the camera unit.

One very preferred embodiment provides that the inversion system has a total of two identical inversion sets A-A made of rod lenses of the type A, one identical inversion set B-B made of two rod lenses of the type B, one mixed inversion set A-B made of one rod lens of each of the type A and the type B, and one further rod lens of the type B. In this case, the inversion system thus has a total of nine rod lenses and four inversion steps. Such an inversion system can accordingly offer a total of five intermediate image planes and/or five conjugated planes, using which the desired relay optical unit may be implemented.

Such an inversion system can thus in particular have a single rod lens at the proximal end which is provided to form a further inversion set with imaging lenses of a camera unit of an endoscope. In such an optical design, a mirror symmetry may be achieved around a center plane of the inversion system, specifically with respect to the number of inversion sets and possibly also with respect to their optical properties such as LCA and TCA.

To achieve the object mentioned at the outset, it is furthermore proposed that the inversion system be used in an endoscope which has an objective and a camera unit as described at the outset. Such an endoscope, which can preferably be designed having a rigid shaft which accommodates the inversion system, can be designed in particular as an oblique view endoscope. The objective of this endoscope can have, for example, one rod lens of a third type C, which differs from the types A and B of the rod lenses used in the inversion system. Even better compensation of optical aberrations may thus be achieved.

Furthermore, it can be provided in particular that the camera of the camera unit of the endoscope, thus the entirety made up of image sensor and associated imaging lenses, is paired with the last rod lens of the inversion system of the above-explained second type B. In this case, this last rod lens is thus arranged in particular proximally and in particular is not associated with any inversion set of the inversion system. Inter alia, this has the advantage that the point of the pupil behind this last rod lens B of the inversion system provides sufficient axial length of the beam path to enable lateral deflection of the beam path, for example, for a 3D endoscope.

Such an endoscope can be chromatically corrected over a broad wavelength range. The use of such an endoscope for fluorescence endoscopy therefore also suggests itself. Fluorescent light, in particular between 815 to 860 nm and/or using excitation light at 808 nm can thus be observed using the endoscope.

BRIEF DESCRIPTION OF THE DRAWINGS

The invention will be described in more detail on the basis of exemplary embodiments but is not restricted to these exemplary embodiments. Further designs of the invention can be obtained from the following description of a preferred exemplary embodiment in conjunction with the general description, the claims, and the drawings.

In the figures.

DETAILED DESCRIPTION

Figure 1:
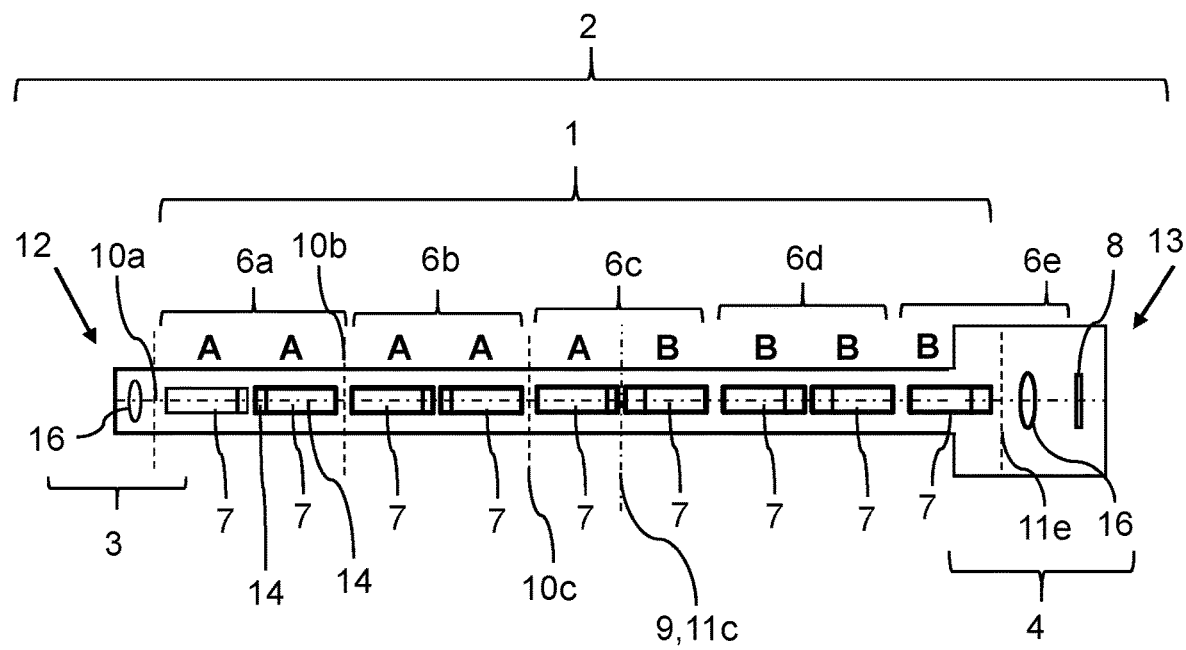
FIG. 1 shows a very schematic illustration of a rigid endoscope according to the invention.

FIG. 1 shows a rigid endoscope 2 identified as a whole with 2, which uses an inversion system 1 according to the invention as a relay optical unit. The inversion system 1 relays light which is collected by an objective 3 of the endoscope 2 at the distal end 12 to the camera unit 4, which is designed as a camera head and has an image sensor 8 and imaging lenses 16 (cf. FIG. 3), at the proximal end 13 of the endoscope 2. More precisely, the inversion system 1, together with the imaging lenses 16 of the camera unit 4, implements imaging of the first intermediate image plane 10*a*, shown at the distal end 12 in FIG. 1, on the image plane of the image sensor 8 at the proximal end 13. By means of the inversion system 1, an image which is produced in a first intermediate image plane 10*a* by the objective 3 (cf. FIG. 2)

is thus transported to the image sensor 8 at the proximal end 13. Repeated image inversion takes place during this relaying.

The inversion system 1 is designed as a rod lens system and has multiple inversion sets 6 arranged in succession, which are sometimes also referred to as inversion steps, since each inversion set 6 implements an approximately 1:1 imaging of a respective distal intermediate image plane 10 to a proximal intermediate image plane 10, wherein a respective image inversion takes place upon this imaging. As illustrated in FIG. 4, the images are thus transported from the intermediate image plane 10a to the next plane 10b, from there to the image plane 10c, and finally to the last intermediate image plane 10e of the inversion system 1. The last rod lens 7 of the type B (at the very bottom in FIG. 4) then transports, together with the optical components P02, P03, L05, L06, and L07 shown in FIG. 3 of the camera unit 4, the image from the plane 10e to the image plane of the image sensor 8.

Figure 2:
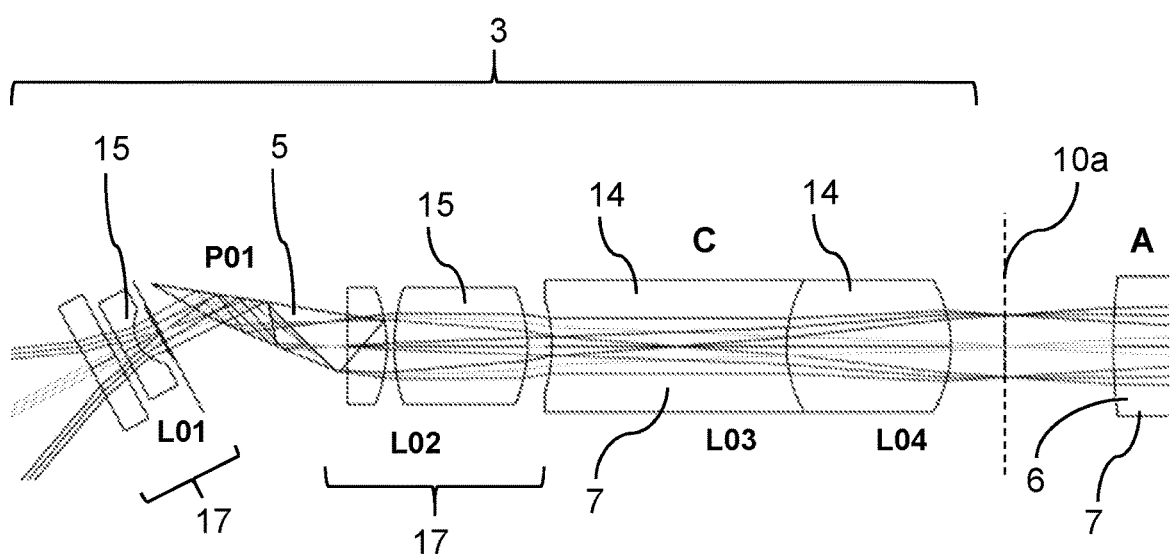
FIG. 2 shows a schematic detail view of the optical components of the objective of the endoscope from FIG. 1.

The individual components of the objective 3 are schematically illustrated in FIG. 2. A first lens group 17 L01 implements, together with the deflection prism 5 P01, an oblique view of the endoscope 2. The second lens group 17 L02 then produces, together with the rod lens 7 of the type C formed from the two lenses L03 and L04, a first image in the first intermediate image plane 10a, which was previously referred to. Moreover, the first rod lens 7 of the type A of the inversion system 1 can be seen at the right-hand edge of FIG. 2. The image in the first intermediate image plane 10a does still show massive chromatic aberrations; however, an image of high color quality then results in the image plane of the image sensor 8 only due to the cooperation with the inversion system 1 and the camera optical unit at the proximal end 13.

While the first aspheric lens 15 of the objective 3 (far left) generates a typically very large negative LCA (due to the concave shape of the lens), primarily the spherical aberration (SA) is controlled using the second aspheric lens 15 L02. Subsequently, the lens pair L03/L04 of the rod lens 7 of the type C ensures image expansion and the generation of an approximately telecentric image.

With the lenses L01 and L03, the objective 3 has two concave lenses here, using which a negative longitudinal chromatic aberration (LCA) can be generated. This can be utilized in particular to compensate at least partially for a positive LCA of the inversion system 1.

Figure 3:
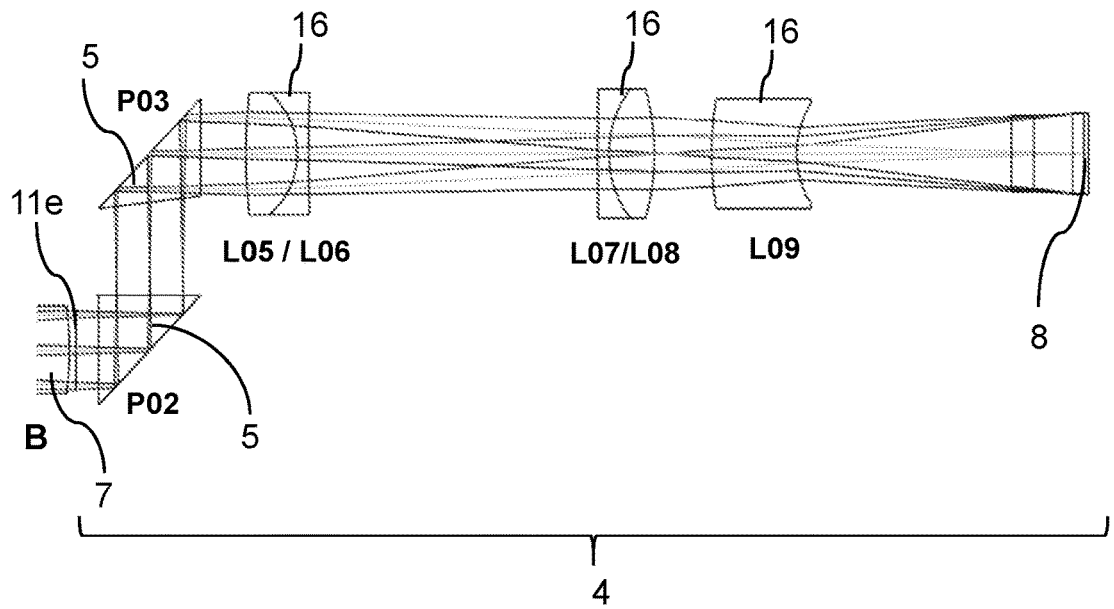
FIG. 3 shows a schematic detail view of the optical components of the camera unit of the endoscope from FIG. 1.
Figure 4:
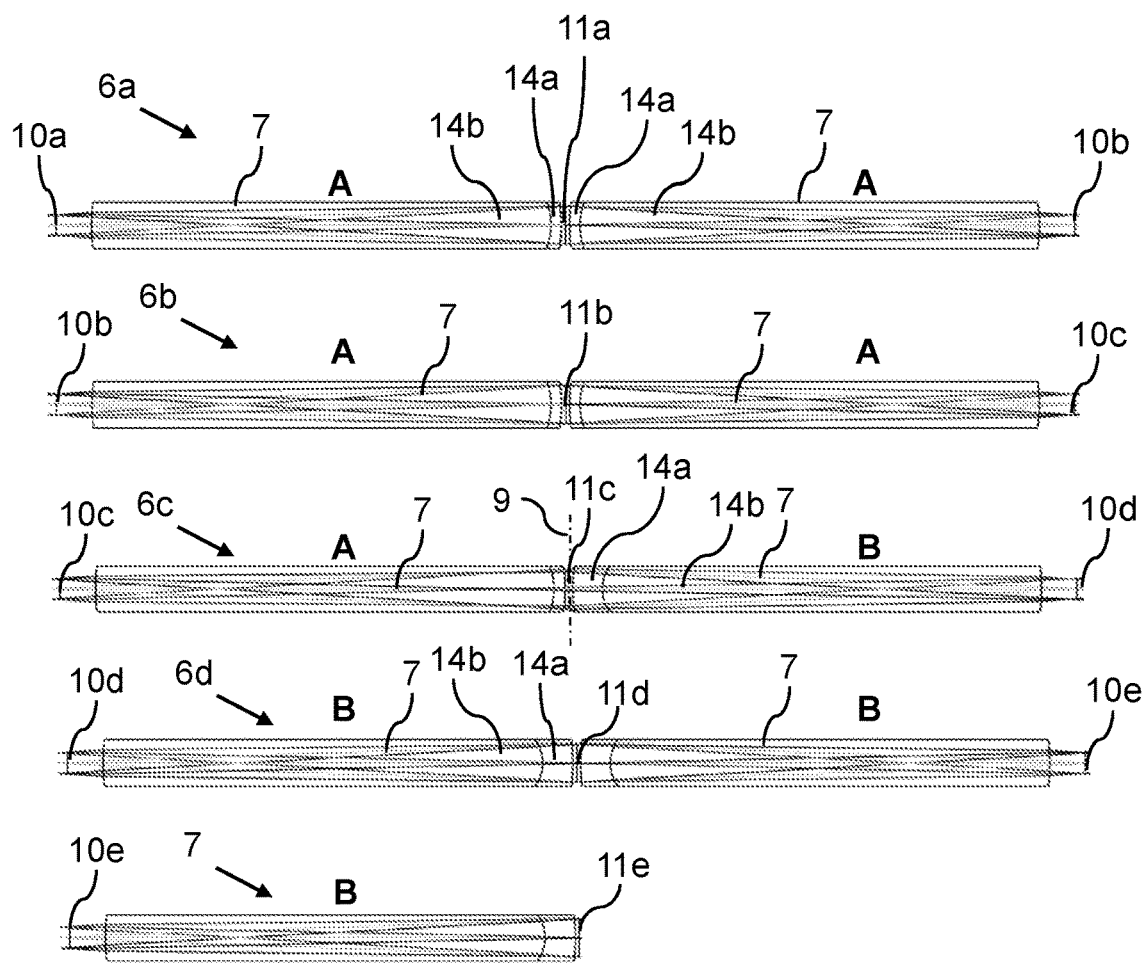
FIG. 4 shows the sequence of inversion sets which form the inversion system shown in FIG. 1 of the endoscope from FIG. 1.

At the proximal end 13 of the endoscope 2, the camera unit 4 having the two concave lenses L05 and L06 also has a possibility of partially compensating for the positive LCA of the inversion system 1 (cf. FIG. 3). Moreover, the beam path is folded by means of two mirror prisms 5. The lenses L05, L06, L07, L08, and L09, in contrast, are paired with the last rod lens 7 of the type B of the inversion system 1, which can be seen at the left-hand edge in FIG. 3, to form an inversion step 6e (cf. FIG. 1).

The individual inversion steps 6a, 6b, 6c, and 6d are shown in detail in FIG. 4 in the correct sequence (from top to bottom) as can be seen in FIG. 1. Each of the four inversion sets 6a, 6b, 6c, 6d (from left to right in FIG. 1) of the inversion system 1 is formed by precisely two rod lenses 7 here, specifically in the combinations A-A, A-A, A-B, and B-B. The inversion system 1 thus has two identical inversion sets 6 A-A made of rod lenses 7 of the type A, one identical inversion set 6 B-B made of two rod lenses 7 of the type B, one mixed inversion set 6 A-B made of one rod lens 7 in each case of the type A and the type B.

In addition, however, the inversion system 1 also has a further single rod lens 7 of the type B at the proximal end 13. This last rod lens 7 of the type B forms, as was already explained, a further inversion set 6e with the imaging lenses 16 of the camera unit 4. A mirror symmetry with respect to the number of inversion sets 6 thus results around the center plane 9, which is illustrated in FIG. 1 and in particular corresponds to the conjugated plane 11c.

As can be seen in FIGS. 1 and 4, only two different types A and B of rod lenses 7 are used in the inversion system 1. These types A and B differ here from the type C of the rod lens 7 which is used in the objective 3. The inversion system 1 thus has a total of nine rod lenses 7 and four inversion steps 6.

Both the rod lenses 7 of the type A and also the rod lenses 7 of the type B are each formed as a doublet (cf. FIG. 4) and thus produce a respective positive longitudinal chromatic aberration (LCA). More precisely, the rod lenses 7 each consist of two complementary glass components 14a, 14b having spheric optical surfaces.

As illustrated in FIG. 4, each rod lens 7 consists of one (long) biconvex lens 14b, on which a (shorter) meniscus lens 14a is placed or cemented. This applies both for rod lenses of the type A and for rod lenses 7 of the type B (cf. FIG. 4), wherein the meniscus lens 14a of the type B is somewhat longer than that of the type A. Accordingly, the biconvex lens 14b of the rod lens 7 of the type B is made somewhat shorter than that of the rod lens 7 of the type A. This approach results in greatly simplified manufacturing of the inversion system 1 and thus in cost savings.

The starting point of the concept according to the invention here is the consideration of forming the rod lenses 7 of the inversion system 1 as cost-effective doublets, which typically generate a positive longitudinal chromatic aberration. Since both the rod lenses 7 of the type A and the rod lenses 7 of the type B use convex lenses, both types A and B fundamentally generate positive longitudinal chromatic aberrations (LCA), which add up along the inversion system 1. The optical design and the material selection for the individual glass components of the rod lenses 7 is then selected in particular so that the identical inversion sets 6 A-A and B-B of the inversion system 1 apply a first longitudinal chromatic aberration (LCA1) and a first transversal chromatic aberration (TCA1) and the mixed inversion set 6 A-B applies a second longitudinal chromatic aberration (LCA2) and a second transversal chromatic aberration (TCA2). The first longitudinal chromatic aberration (LCA1) and the second longitudinal chromatic aberration (LCA2) have the same sign here and the first transversal chromatic aberration (TCA1) and the second transversal chromatic aberration (TCA2) have different signs. As a result, the transversal chromatic aberrations of the individual inversion sets 6 at least partially compensate for one another, while the longitudinal chromatic aberrations thereof add up.

In summary, to improve the imaging with simultaneous simplification of the manufacturing of a rigid endoscope 2, it is proposed that an inversion system 1 be used as a relay optical unit for the image transfer from an objective 3 to a proximally arranged camera unit 4 of the endoscope 2, which inversion system has an odd number of a first type A of rod lenses 7 and an even number of a second type B of rod lenses 7, which are each arranged on half of the inversion system 1 in relation to a center plane 9 of the inversion system 1 (cf. FIG. 1).

LIST OF REFERENCE NUMERALS 1 inversion system
2 endoscope 3 objective
4 camera unit
5 deflection prism
6 inversion set/inversion step
7 rod lens
8 image sensor
9 center plane (symmetry plane)
10 intermediate image plane
11 conjugated plane
12 distal end (of 2 or 1)
13 proximal end (of 2 or 1)
14 component (of 7)
15 aspheric lens
16 imaging lenses
17 lens group

The invention claimed is:

1. An inversion system (1) for use in an endoscope (2), which has an objective (3) and a camera unit (4), the inversion system (1) being configured to relay light from the objective (3) to the camera unit (4) and comprising:
multiple inversion sets (6) each made up of two rod lenses (7), which each implement approximately 1:1 imaging, wherein there is only has a first type A and a second type B of the rod lenses (7),
a respective one of the inversion sets (6) A-A or B-B, which is formed from two of the rod lenses (7) of the same type, applies a first longitudinal chromatic aberration (LCA1) and a first transversal chromatic aberration (TCA1) and
one of the inversion sets (6) A-B of the inversion system (1), which is formed from two of the rod lenses (7) of different types, applies a second longitudinal chromatic aberration (LCA2) and a second transversal chromatic aberration (TCA2),
the first longitudinal chromatic aberration (LCA1) and the second longitudinal chromatic aberration (LCA2) have a same sign, and
the first transversal chromatic aberration (TCA1) and the second transversal chromatic aberration (TCA2) have different signs, and
the transversal chromatic aberrations of the individual inversion sets (6) partially compensate for one another, while the longitudinal chromatic aberrations thereof add up.

2. The inversion system (1) according to claim 1, wherein the respective longitudinal chromatic aberrations (LCA1) and the respective transversal chromatic aberrations (TCA1) of the inversion sets (6) A-A or B-B which are each formed from two of the rod lenses (7) of the same type, have the same sign.

3. The inversion system (1) according to claim 1, wherein one of the inversions set (6) B-B which is formed from two of the rod lenses (7) of the second type B, applies a third longitudinal chromatic aberration (LCA3), which is less in absolute value than at least one of the second longitudinal chromatic aberration (LCA2) or the first longitudinal chromatic aberration (LCA1).

4. The inversion system (1) according to claim 1, wherein one of the inversion sets (6) B-B which is formed from two of the rod lenses (7) of the second type B, applies a third transversal chromatic aberration (TCA3), which is less in absolute value than at least one of the second transversal chromatic aberration (TCA2) or the first transversal chromatic aberration (TCA1).

5. The inversion system (1) according to claim 1, wherein the transversal chromatic aberrations (TCA) of a mixed inversion step (6) A-B and of a further inversion step (6) B-B, which is formed from two of the rod lenses of the type B, have the same sign, and the transversal chromatic aberration (TCA) of an inversion step (6) A-B, which is formed from two of the rod lenses of different types, is less than that of an inversion step (6) A-A, which is formed from two of the rod lenses of the type A.

6. The inversion system (1) according to claim 1, wherein all the rod lenses (7) are each formed as doublets with only two different components (14a, 14b), such that the rod lenses (7) all apply a positive longitudinal chromatic aberration (LCA1, LCA2, LCA3), and a total longitudinal chromatic aberration of the inversion system (1) is positive.

7. The inversion system (1) according to claim 1, wherein there is an odd number of the rod lenses (7) of the first type A.

8. The inversion system (1) according to claim 1, wherein there is an even number of the rod lenses (7) of the second type B.

9. The inversion system (1) according to claim 1, wherein there is a total of
two identical ones of the inversion sets (6) A-A made up of the rod lenses (7) of the type A,
one of the inversion sets (6) B-B made up of two of the rod lenses (7) of the type B,
one mixed one of the inversion sets (6) A-B made up of one of the rod lenses (7) each of the type A and of the type B, and
one further one of the rod lenses (7) of the type B,
to form a total of five intermediate image planes (10a, 10b, 10c, 10d, 10e), five conjugated planes (11a, 11b, 11c, 11d, 11e), or five intermediate image planes (10a, 10b, 10c, 10d, 10e) and five conjugated planes (11a, 11b, 11c, 11d, 11e).

10. The inversion system (1) according to claim 1, further comprising
a single one of the rod lenses (7) at a proximal end (13), which is provided to form a further inversion set (6e) with imaging lenses (16) of the camera unit (4),
such that overall a mirror symmetry with respect to a number of the inversion sets (6) results around a center plane (9) of the inversion system (1).

11. An endoscope (2) comprising an objective (3), a camera unit (4), and the inversion system (1) of claim 1 arranged between the objective (3) and the camera unit (4).

12. The endoscope of claim 11, wherein the endoscope is an oblique view endoscope (2).

13. The endoscope of claim 11, wherein the objective (3)) has a rod lens (7) of a type C, which deviates from the types A and B of the rod lenses (7) in the inversion system (1).

14. A method of using the endoscope of claim 11, comprising:
observing fluorescent light between 815 to 860 nm with the endoscope.

15. The method of claim 14, further comprising using excitation light at 808 nm.

* * * * *